United States Patent
Shimizu et al.

(10) Patent No.: US 10,016,353 B2
(45) Date of Patent: Jul. 10, 2018

(54) HAIR COSMETIC COMPOSITION

(71) Applicant: HOYU CO., LTD., Nagoya-shi (JP)

(72) Inventors: Kaori Shimizu, Aichi-ken (JP); Nana Morishita, Aichi-ken (JP)

(73) Assignee: HOYU CO., LTD., Nagoya-shi (JP)

( * ) Notice: Subject to any disclaimer, the term of this patent is extended or adjusted under 35 U.S.C. 154(b) by 0 days.

(21) Appl. No.: 15/602,337

(22) Filed: May 23, 2017

(65) Prior Publication Data

US 2017/0340546 A1  Nov. 30, 2017

(30) Foreign Application Priority Data

May 25, 2016 (JP) ................................. 2016-103911

(51) Int. Cl.

| | | |
|---|---|---|
| *A61Q 5/10* | (2006.01) | |
| *A61K 8/73* | (2006.01) | |
| *A61K 8/19* | (2006.01) | |
| *A61K 8/22* | (2006.01) | |
| *A61K 8/31* | (2006.01) | |
| *A61K 8/34* | (2006.01) | |
| *A61K 8/41* | (2006.01) | |
| *A61K 8/86* | (2006.01) | |
| *A61Q 5/08* | (2006.01) | |
| *A61K 8/39* | (2006.01) | |

(52) U.S. Cl.
CPC ................ *A61K 8/731* (2013.01); *A61K 8/19* (2013.01); *A61K 8/22* (2013.01); *A61K 8/31* (2013.01); *A61K 8/342* (2013.01); *A61K 8/39* (2013.01); *A61K 8/41* (2013.01); *A61K 8/86* (2013.01); *A61Q 5/08* (2013.01); *A61Q 5/10* (2013.01); *A61K 2800/882* (2013.01)

(58) Field of Classification Search
CPC .......... A61K 8/731; A61K 8/86; A61K 8/342; A61K 8/31; A61K 8/22; A61K 8/41; A61K 2800/882; A61Q 5/10
See application file for complete search history.

(56) References Cited

U.S. PATENT DOCUMENTS 6,379,400 B1 * 4/2002 Braun .................... A61K 8/418
8/415

FOREIGN PATENT DOCUMENTS

| JP | 2005-089307 A | 4/2005 |
|---|---|---|
| JP | 2007-126415 A | 5/2007 |

* cited by examiner

*Primary Examiner* — Eisa B Elhilo
(74) *Attorney, Agent, or Firm* — Posz Law Group, PLC

(57) ABSTRACT

A hair cosmetic composition includes an alkaline agent and an oxidant, and is constituted as a hair dye or a hair bleaching/dye removing agent. The hair cosmetic composition further includes (A) a cellulose derivative and (B) a polyethylene glycol having a number average molecular weight of 2,000 or less. The mass ratio of the content of the (B) component to the content of the (A) component is 1 to 50.

4 Claims, No Drawings

HAIR COSMETIC COMPOSITION

BACKGROUND OF THE INVENTION

The present invention relates to a hair cosmetic composition comprising an alkaline agent and an oxidant, and constituted as a hair dye or a hair bleaching/dye removing agent.

In general, as a hair cosmetic composition, there has been known a hair dye or a hair bleaching/dye removing agent exhibiting effects by mixing different types of chemicals. As such a hair cosmetic composition, for example, there has been known an oxidative hair dye composed of a first agent containing an alkaline agent and an oxidative dye, and a second agent containing an oxidant such as hydrogen peroxide. The alkaline agent promotes the action of the oxidant contained in the second agent, and also improves the hair-dyeing power by swelling hair so as to improve the permeability of the dye into the hair.

The hair cosmetic composition is prepared as a mixture by mixing different types of chemicals when used, and then applied to hair by using a brush, a comb or the like. There have hitherto been known a hair cosmetic composition containing a cellulose derivative for the purpose of improving the spreadability of the mixture and improving the application property to hair when the composition is applied to hair by using a brush or the like. For example, the hair cosmetic compositions of Japanese Laid-Open Patent Publication No. 2005-089307 and Japanese Laid-Open Patent Publication No. 2007-126415 contain a hydroxyalkyl cellulose or a cationized cellulose.

SUMMARY OF THE INVENTION

However, a hair cosmetic composition containing a cellulose derivative suffers from a problem that when the moisture of the composition is evaporated during use, the application property of the composition is remarkably degraded over time.

An objective of the present invention is to provide a hair cosmetic composition that is constituted as a hair dye or a hair bleaching/dye removing agent, contains a cellulose derivative, and is capable of suppressing the degradation of the application property thereof.

The present invention is based on the finding that the degradation of the application property of the hair cosmetic composition is suppressed by mixing a predetermined amount of a polyethylene glycol having a predetermined molecular weight. The numerical values representing the contents of the components in terms of percent by mass are the numerical values in a formulation including a solubilizer such as water.

To achieve the foregoing objective and in accordance with one aspect of the present invention, a hair cosmetic composition is provided that comprises an alkaline agent and an oxidant, and is constituted as a hair dye or a hair bleaching/dye removing agent. The hair cosmetic composition further comprises (A) a cellulose derivative and (B) a polyethylene glycol having a number average molecular weight of 2,000 or less. The mass ratio of the content of the (B) component to the content of the (A) component is 1 to 50.

The hair cosmetic composition may further include (C) at least one oily component that is in a liquid state at 25° C. and is selected from the group consisting of a higher alcohol, an oil/fat, a hydrocarbon, a higher fatty acid, and a wax. The (C) component may include a higher alcohol that is in a liquid state at 25° C. The hair cosmetic composition may include a first agent containing the alkaline agent and the (A) component, and a second agent containing the oxidant. The hair cosmetic composition may be applied to hair after the first agent and the second agent are shaken and mixed with each other in an airtight container.

Other aspects and advantages of the present invention will become apparent from the following detailed description illustrating by way of example the principles of the present invention.

DETAILED DESCRIPTION OF THE PREFERRED EMBODIMENTS

Hereinafter, a hair cosmetic composition according to one embodiment of the present invention will be described. In this embodiment, the hair cosmetic composition is a two-part type oxidative hair dye will be described. The two-part type oxidative hair dye is composed of a first agent and a second agent, and is used for dyeing hair after the first agent and the second agent are mixed with each other. Alternatively, the oxidative hair dye may also be constituted as a three-part type oxidative hair dye.

<Two-Part Type Oxidative Hair Dye>

The two-part type oxidative hair dye is composed of, for example, a first agent containing an alkaline agent and an oxidative dye, and a second agent containing an oxidant and the like.

(First Agent of Two-Part Type Oxidative Hair Dye)

The first agent contains, in addition to the alkaline agent and the oxidative dye, for example, (A) a cellulose derivative, (B) a polyethylene glycol having a number average molecular weight of 2,000 or less, and (C) at least one oily component that is in a liquid state at 25° C. and is selected from a higher alcohol, an oil/fat, a hydrocarbon, a higher fatty acid and a wax.

(A) A cellulose derivative improves the spreadability of the mixture, and improves the application property to hair when the composition is applied to hair by using a brush or the like. The cellulose derivative also improves the miscibility when different types of chemicals are mixed with each other. Specific examples of (A) the cellulose derivative include methyl cellulose, ethyl cellulose, hydroxyethyl cellulose, hydroxypropyl cellulose, carboxymethyl cellulose, sodium carboxymethyl cellulose, hydroxypropyl methyl cellulose, and a cationized cellulose derivative. Specific examples of the cationized cellulose derivative include: a polymer of a quaternary ammonium salt obtained by adding glycidyl trimethyl ammonium chloride to hydroxy ethyl cellulose (polyquaternium-10 (INCI name): such as Leogard G and Leogard GP (manufactured by Lion Corp.), Polymer JR-125, Polymer JR-400, Polymer JR-30M, Polymer LR-400 and Polymer LR-30M (manufactured by Amerchol, Inc.), Celquat SC-230M (manufactured by AkzoNobel Inc.)), hydroxy ethyl cellulose/dimethyl diallyl ammonium chloride copolymer (polyquaternium-4: such as Celquat H-100 and Celquat L-200 (manufactured by AkzoNobel Inc.)). Among these, only one derivative may be contained alone, or two or more derivatives may be contained in combination. Among these, from the viewpoint of being excellent in the miscibility and the application property, a hydroxyalkyl cellulose or a derivative thereof are preferable, and hydroxyethyl cellulose is more preferable.

In the hair cosmetic composition, namely, in the mixture of the first agent and the second agent, the lower limit of the content of (A) the cellulose derivative is appropriately set, and is preferably 0.01% by mass or more, more preferably 0.1% by mass or more, and furthermore preferably 0.15% by mass or more. When the content of (A) the cellulose derivative is 0.01% by mass or more, the spreadability of the hair cosmetic composition is improved.

In the mixture of the first agent and the second agent, the upper limit of the content of (A) the cellulose derivative is appropriately set, and is preferably 1% by mass or less, more preferably 0.75% by mass or less, and furthermore preferably 0.5% by mass or less. When the content of (A) the cellulose derivative is 1% by mass or less, the solubility in the composition is improved.

(B) The polyethylene glycol having a predetermined molecular weight suppresses the degradation with time of the application property of the hair cosmetic composition. The upper limit of the number average molecular weight of (B) the polyethylene glycol is 2,000 or less, preferably 1,600 or less, and more preferably 1,000 or less. When the number average molecular weight is set to be 2,000 or less, the degradation of the application property is suppressed. The lower limit of the number average molecular weight of (B) the polyethylene glycol is not particularly limited, but is preferably 100 or more from the viewpoint of the easy availability of the raw materials.

The lower limit of the content of the (B) component in the mixture of the first agent and the second agent is appropriately set, and is preferably 0.1% by mass or more, more preferably 0.5% by mass or more, and furthermore preferably 1% by mass or more. When the content of the (B) component is 0.1% by mass or more, the degradation with time of the application property of the hair cosmetic composition can be suppressed.

The upper limit of the content of the (B) component in the mixture of the first agent and the second agent is appropriately set, and is preferably 10% by mass or less, more preferably 7% by mass or less, and furthermore preferably 5% by mass or less. When the content of the (B) component is 10% by mass or less, the hair dyeing property is improved.

The lower limit of the mass ratio of the content of the (B) component to the content of the (A) component in the mixture of the first agent and the second agent is 1 or more, preferably 3 or more, and more preferably 5 or more. When the mass ratio is set to be 1 or more, the degradation with time of the application property of the hair cosmetic composition is suppressed. The upper limit of the mass ratio of the content of the (B) component to the content of the (A) component in the mixture of the first agent and the second agent is 50 or less, preferably 40 or less, and more preferably 30 or less. When the mass ratio is set to be 50 or less, the hair dyeing property is improved.

The (C) component enhances the suppression of degradation with time of the application property of the hair cosmetic composition. Accordingly, the hair cosmetic composition preferably includes the (C) component. The (C) component is at least one selected from a higher alcohol that is in the liquid state at 25° C., an oil/fat that is in the liquid state at 25° C., hydrocarbon that is in the liquid state at 25° C., a higher fatty acid that is in the liquid state at 25° C., and a wax that is in the liquid state at 25° C. Specific examples of the higher alcohol that is in the liquid state at 25° C. include isostearyl alcohol, 2-octyldodecanol, decyltetradecanol, oleyl alcohol, 2-hexyldecanol, and lauryl alcohol. Specific examples of the oil/fat that is in the liquid state at 25° C. include Argania spinosa kernel oil, olive oil (purified olive oil), camellia oil, tea seed oil, camellia oleifera seed oil, safflower oil, sunflower oil, soybean oil, cottonseed oil, sesame oil, corn oil, peanut oil, rapeseed oil, rice bran oil, rice germ oil, wheat germ oil, tear grass oil, grape seed oil, almond oil, avocado oil, carrot oil, macadamia nut oil, castor oil, linseed oil, coconut oil, evening primrose oil, mink oil and egg-yolk oil. Specific examples of the hydrocarbon that is in the liquid state at 25° C. include α-olefin oligomer, light isoparaffin, light liquid isoparaffin, synthetic squalane, vegetable squalane, squalane, polybutene, liquid isoparaffin, and liquid paraffin. Specific examples of the higher fatty acid that is in the liquid state at 25° C. include isostearic acid and oleic acid. Specific examples of the wax that is in the liquid state at 25° C. include jojoba oil. Among these, only one may be contained alone, or two or more thereof may be contained in combination. Among these, camellia oil, sunflower oil and castor oil are preferable as the oil/fat that is in the liquid state; α-olefin oligomer, light isoparaffin, and light liquid isoparaffin are preferable as the hydrocarbon that is in the liquid state; and oleic acid is preferable as the higher fatty acid that is in the liquid state. Moreover, from the viewpoint of being excellent in the formulation stability, a higher alcohol that is in the liquid state at 25° C. is preferable.

The lower limit of the content of the (C) component in the mixture of the first agent and the second agent is appropriately set, and is preferably 0.01% by mass or more, more preferably 0.1% by mass or more, and furthermore preferably 0.15% by mass or more. When the content of the (C) component is 0.01% by mass or more, the degradation with time of the application property is more suppressed. The upper limit of the content of the (C) component in the mixture of the first agent and the second agent is appropriately set, and is preferably 20% by mass or less, more preferably 15% by mass or less, and furthermore preferably 10% by mass or less. When the content of the (C) component is 20% by mass or less, the formulation stability is more improved.

The lower limit of the content of the (C) component in the total mass of the contents of a higher alcohol(s), an oil(s)/fat(s), a hydrocarbon(s), a higher fatty acid(s), and a wax(es) in the mixture of the first agent and the second agent is appropriately set, and is preferably 3% by mass or more, more preferably 5% by mass or more, and furthermore preferably 7% by mass or more. When the content of the (C) component in such a total mass is 3% by mass or more, the degradation with time of the application property is more suppressed.

The alkaline agent contained in the first agent acts to improve the hair dyeing effect by promoting the action of the oxidant contained in the second agent. Examples of the alkaline agent include ammonia, an alkanolamine, a silicate, a carbonate, a hydrogencarbonate, a metasilicate, a sulfate, a chloride, a phosphate, an organic amine, a basic amino acid, and a hydroxide of an alkali metal or an alkaline earth metal. Specific examples of the alkanolamine include monoethanolamine and triethanolamine. Specific examples of the silicate include sodium silicate and potassium silicate. Specific examples of the carbonate include sodium carbonate and ammonium carbonate. Specific examples of the hydrogencarbonate include sodium hydrogencarbonate and ammonium hydrogencarbonate. Specific examples of the metasilicate include sodium metasilicate and potassium metasilicate. Specific examples of the sulfate include ammonium sulfate. Specific examples of the chloride include ammonium chloride. Specific examples of the phosphate include ammonium dihydrogenphosphate and diammonium hydrogenphosphate. Specific examples of the organic amine include 2-amino-2-methyl-1-propanol (AMP), 2-amino-2-methyl-1,3-propanediol, and guanidine. Specific examples of the basic amino acid include arginine and lysine. Specific examples of the hydroxide of an alkali metal or an alkaline earth metal include sodium hydroxide and potassium hydroxide. Only one of these alkaline agents may be contained alone, or two or more of these alkaline agents may be contained in combination. Among these, from the viewpoint of improving the hair dyeing effect, ammonia, an ammonium salt, and an alkanolamine are preferably applied.

The content of the alkaline agent in the mixture of the first agent and the second agent is preferably such that the alkaline agent is mixed in such a way that the pH of the mixture falls within a range between 7 and 12. By regulating the pH of the mixture of the first agent and the second agent so as to be 7 or more, the action of the oxidant contained in the second agent is more promoted. By regulating the pH of the mixture of the first agent and the second agent so as to be 12 or less, the damage of hair due to the application of the oxidative hair dye is more suppressed.

The oxidative dye is a compound capable of developing a color due to the oxidation polymerization caused by the oxidant contained in the second agent, and is classified into a dye intermediate and a coupler, and the oxidative dye preferably includes a dye intermediate and a coupler.

Examples of the dye intermediate include p-phenylenediamine, toluene-2,5-diamine (p-toluylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chloro-p-phenylenediamine, 4-amino-m-cresol, 2-amino-4-hydroxyethylaminoanisole, 2,4-diaminophenol, and a salt thereof. Specific examples of the salt include a hydrochloride and a sulfate. Only one of these specific examples of the dye intermediate may be contained alone, or two or more of these specific examples of the dye intermediate may be contained in combination.

The coupler develops a color by bonding to the dye intermediate. Examples of the coupler include resorcin, 5-amino-o-cresol, m-aminophenol, α-naphthol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, 1,5-dihydroxynaphthalene, and a salt thereof. Specific examples of the salt include a hydrochloride and a sulfate. Only one of these specific examples of the coupler may be contained alone, or two or more of these specific examples of the coupler may be contained in combination. The oxidative dye is preferably composed of at least one selected from the specific examples of the dye intermediate and at least one selected from the specific examples of the coupler from the viewpoint of providing variations of hair color tone. The first agent may optionally contain, as the dyes other than the aforementioned oxidative dyes, the oxidative dyes listed in, for example, "The Japanese Standards of Quasi-Drug Ingredients" (published by Yakuji Nippo Ltd., June 2006).

The lower limit of the content of the oxidative dye in the mixture of the first agent and the second agent is appropriately set, and is preferably 0.01% by mass or more, more preferably 0.1% by mass or more, and furthermore preferably 0.5% by mass or more. When the content of the oxidative dye is 0.01% by mass or more, the hair-dyeing power among other things is more improved.

The upper limit of the content of the oxidative dye in the mixture of the first agent and the second agent is appropriately set, and is preferably 10% by mass or less, more preferably 7% by mass or less, and furthermore preferably 5% by mass or less. When the content of the oxidative dye is 10% by mass or less, in particular in the case where a solubilizer is used, the solubility to the solubilizer is improved.

The oxidative hair dye may further contain, if necessary, the components other than the foregoing components such as a solubilizer, a water-soluble polymer other than the foregoing water soluble polymers, an oily component other than the foregoing oily components, a polyhydric alcohol other than the foregoing polyhydric alcohols, a surfactant, a pH adjuster, a sugar, a preservative, a stabilizer, a plant extract, a crude drug extract, a vitamin, a perfume, an antioxidant, a chelating agent, and an ultraviolet absorber.

A solubilizer is mixed, for example, in the case where the first agent is made in a liquid form. Examples of the solubilizer used include water and an organic solvent. Specific examples of the organic solvent include ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anise alcohol, p-methylbenzyl alcohol, α-dimethyl phenethyl alcohol, α-phenylethanol, ethylene glycol phenyl ether (phenoxyethanol), phenoxyisopropanol, 2-benzyloxyethanol, an N-alkylpyrrolidone, an alkylene carbonate, and an alkyl ether. Only one of these solubilizers may be contained alone, or two or more of these solubilizers may be contained in combination. Among these, water is preferably applied because water is excellent in the capability of dissolving the other components in the first agent. When water is used as the solvent, the content of water in the mixture of the first agent and the second agent (the content at the time of use) is preferably 40% by mass or more and more preferably 50% by mass or more.

A water-soluble polymer imparts an appropriate viscosity to the oxidative hair dye. Accordingly, the oxidative hair dye may contain a water-soluble polymer within a range not impairing the advantageous effects of the present invention. Examples of the water-soluble polymer include a natural polymer, a semisynthetic polymer, a synthetic polymer, and an inorganic polymer. Specific examples of the natural polymer include guar gum, locust bean gum, quince seed, carrageenan, galactan, gum arabic, tragacanth gum, pectin, mannan, xanthan gum, dextran, succinoglucan, curdlan, hyaluronic acid, gelatin, casein, albumin, collagen, dextrin, and triglucopolysaccharide (pullulan).

Specific examples of the semisynthetic polymer include cationized guar gum, starch phosphate, propylene glycol alginate, and an alginic acid salt. Specific examples of the synthetic polymer include polyvinyl caprolactam, polyvinyl alcohol (PVA), polyvinylpyrrolidone (PVP), vinylpyrrolidone-vinyl acetate (VP/VA) copolymer, polyvinyl butylal, polyvinyl methyl ether, carboxyvinyl polymer, sodium polyacrylate, polyacrylamide, polyethylene oxide, ethylene oxide-propylene oxide block copolymer, acrylic acid/alkyl acrylate copolymer, polydimethylmethylene piperidinium chloride, and a copolymer composed of a semi-ester of itaconic acid and polyoxyethylene (hereinafter, referred to as "POE") alkyl ether, or an ester of methacrylic acid and a POE alkyl ether, and at least one monomer selected from acrylic acid, methacrylic acid and alkyl esters of these acid. Only one of these water-soluble polymers may be contained alone, or two or more of these water-soluble polymers may be contained in combination.

The oily component imparts a moist feeling to hair. Accordingly, the oxidative hair dye may contain an oily component within a range not impairing the advantageous effects of the present invention. Examples of the oily component include an oil/fat that is in the solid state at 25° C., a wax that is in the solid state at 25° C., a higher alcohol that is in the solid state at 25° C., a hydrocarbon that is in the solid state at 25° C., a higher fatty acid that is in the solid state at 25° C., an alkyl glyceryl ether, an ester, and silicone.

Specific examples of the oil/fat that is in the solid state at 25° C. include lanolin, shea fat, beef tallow, horse fat, hydrogenated egg yolk fat, cacao fat, palm fat, hydrogenated palm kernel fat, hydrogenated castor oil, and theobroma grandiflorum seed butter. Specific examples of the wax that is in the solid state at 25° C. include beeswax, candelilla wax, carnauba wax, lanolin wax, rice bran wax, sugarcane wax, insect white wax, palm wax, and montan wax. Specific examples of the higher alcohol that is in the solid state at 25° C. include cetyl alcohol (cetanol), stearyl alcohol, cetostearyl alcohol, arachidyl alcohol, behenyl alcohol, myristyl alcohol, and lanolin alcohol. Specific examples of the hydrocarbon that is in the solid state at 25° C. include paraffin, polyethylene, microcrystalline wax, vaseline, ozokerite, and ceresin. Specific examples of the higher fatty acid that is in the solid state at 25° C. include lauric acid, myristic acid, palmitic acid, stearic acid, behenic acid, 12-hydroxystearic acid, and lanolin fatty acid.

Specific examples of the alkyl glyceryl ether include batyl alcohol, chimyl alcohol, selachyl alcohol, and isostearyl glyceryl ether. Specific examples of the ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a fatty acid cholesteryl/lanosteryl having 10 to 30 carbon atoms, cetyl lactate, lanolin acetate, ethylene glycol di-2-ethylhexanoate, pentaerythritol fatty acid ester, dipentaerythritol fatty acid ester, cetyl caprate, glyceryl tricaprylate, diisostearyl malate, dioctyl succinate, and cetyl 2-ethyl hexanoate.

Specific examples of the silicone include dimethylpolysiloxane (dimethicone), methylphenylpolysiloxane, decamethylcyclopentasiloxane, dodecamethylcyclohexasiloxane, a terminal hydroxyl group-modified dimethylpolysiloxane, a high polymerization silicone, a polyether-modified silicone (for example, (PEG/PPG/butylene/dimethicone) copolymer), an amino-modified silicone, a betaine-modified silicone, an alkyl-modified silicone, an alkoxy-modified silicone, a mercapto-modified silicone, a carboxy-modified silicone, and a fluorine-modified silicone. Only one of these oily components may be contained alone, or two or more of these oily components may be contained in combination.

Examples of the polyhydric alcohol include a glycol and glycerin. Examples of the glycol include ethylene glycol, a polyethylene glycol having an number average molecular weight exceeding 2,000, high-polymerization polyethylene glycol, propylene glycol, dipropylene glycol, polypropylene glycol, isoprene glycol, and 1,3-butylene glycol. Examples of the glycerin include glycerin, diglycerin, and polyglycerin. Only one of these polyhydric alcohols may be contained alone, or two or more of these polyhydric alcohols may be contained in combination.

The surfactant, as an emulsifying agent or a component for solubilizing the respective components, emulsifies or solubilizes the oxidative hair dye, and regulates the viscosity of the oxidative hair dye and improves the viscosity stability of the oxidative hair dye when the oxidative hair dye is used. Accordingly, the oxidative hair dye may contain a surfactant within a range not impairing the advantageous effects of the present invention. Examples of the surfactant include an anionic surfactant, a cationic surfactant, an amphoteric surfactant, and a nonionic surfactant.

Specific examples of the anionic surfactant include an alkyl ether sulfate, an alkyl sulfate, an alkyl ether sulfate ester salt, an alkenyl ether sulfate, an alkenyl sulfate, an olefin sulfonate, an alkane sulfonate, a saturated or unsaturated fatty acid salt, an alkyl or alkenyl ether carboxylate, an α-sulfofatty acid salt, an N-acylamino acid-type surfactant, a phosphate mono- or di-ester-type surfactant, a sulfosuccinic acid ester, an N-alkyloylmethyl taurine salt, and a drivative thereof. Specific examples of the counterion of the anionic group of these surfactants include sodium ion, potassium ion, and triethanolamine. More specifically, examples of the alkyl ether sulfate ester salt include sodium POE lauryl ether sulfate. Specific examples of the alkyl sulfate include sodium lauryl sulfate and sodium cetyl sulfate. Specific examples of the derivative of the alkyl sulfate include sodium POE lauryl sulfate. Specific examples of the sulfosuccinic acid ester include disodium lauryl sulfosuccinate. Specific examples of the N-alkyloylmethyl taurine salt include sodium N-stearoyl-N-methyltaurate.

Specific examples of the cationic surfactant include lauryl trimethyl ammonium chloride, cetyl trimethyl ammonium chloride, stearyl trimethyl ammonium chloride, alkyl trimethyl ammonium chloride, distearyl dimethyl ammonium chloride, cetyl trimethyl ammonium bromide, stearyl trimethyl ammonium bromide, lanolin fatty acid aminopropyl ethyl dimethyl ammonium ethyl sulfate, stearyl trimethyl ammonium saccharin, cetyl trimethyl ammonium saccharin, methacryloyloxy ethyl trimethylammonium chloride, behenyl trimethyl ammonium methyl sulfate, behenyl dimethyl amine, behenic acid diethyl aminoethyl amide, behenic acid dimethyl aminopropyl amide, behenic acid dimethyl aminoethyl amide, stearyl dimethyl amine, palmitoxypropyl dimethylamine, stearoxypropyl dimethylamine, and stearic acid dimethyl aminopropyl amide. Specific examples of the alkyl trimethyl ammonium chloride include behenyl trimethyl ammonium chloride and arachidyl trimethyl ammonium chloride.

Specific examples of the amphoteric surfactant include coco-betaine, lauramidopropyl betaine, cocamidopropyl betaine, sodium lauroamphoacetate, sodium cocoamphoacetate, coconut oil fatty acid amidopropyl betaine, lauryl betaine (betaine lauryldimethylamino acetate), and sodium laurylaminopropionate.

Specific examples of the nonionic surfactant include an ether-type nonionic surfactant, an ester-type nonionic surfactant, and an alkyl glucoside. Specific examples of the ether-type nonionic surfactant include POE cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, POE polyoxypropylene cetyl ether, and POE polyoxypropylene decyl tetradecyl ether.

Specific examples of the ester-type nonionic surfactant include POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbit tetraoleate, POE sorbit hexastearate, POE sorbit monolaurate, POE sorbit bees wax, polyethylene glycol monooleate, polyethylene glycol monostearate, polyethylene glycol monolaurate, lipophilic glycerin monooleate, lipophilic glycerin monostearate, self-emulsifying glycerin monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Specific examples of the alkyl glucoside include an alkyl (having 8 to 16 carbon atoms) glucoside, POE methyl glucoside, and POE methyl glucoside dioleate. Only one of these specific examples of the surfactant may be contained alone, or two or more of these specific examples of the surfactant may be contained in combination.

The pH adjuster may be mixed in order to adjust the pH of the oxidative hair dye. The pH adjuster may be selected from the known pH adjusters. Examples of the pH adjuster include an inorganic acid, an organic acid, and a salt thereof. Specific examples of the organic acid include citric acid, glycolic acid, succinic acid, tartaric acid, lactic acid, malic acid, levulinic acid, acetic acid, butyric acid, valeric acid, oxalic acid, maleic acid, fumaric acid, and mandelic acid. Specific examples of the organic acid salt include a sodium salt, a potassium salt, and an ammonium salt. Specific examples of the inorganic acid include phosphoric acids such as phosphoric acid and pyrophosphoric acid, hydrochloric acid, sulfuric acid, and nitric acid. These may be used each alone, or in combinations of two or more thereof.

Specific example of the sugar include: monosaccharides such as glucose and galactose; disaccharides such as maltose, sucrose, fructose, and trehalose; and a sugar alcohol. Specific examples of the preservative include paraben, methylparaben, and sodium benzoate. Specific examples of the stabilizer include phenacetin, 8-hydroxyquinoline, acetanilide, sodium pyrophosphate, barbituric acid, uric acid, and tannic acid. Specific examples of the antioxidant include ascorbic acids and sulfites. Specific examples of the chelating agent include edetic acid (ethylenediaminetetraacetic acid (EDTA)), disodium edetate, tetrasodium edetate, diethylenetriaminepentaacetic acid and salts thereof, ethylenediaminehydroxyethyl triacetic acid and salts thereof, and hydroxyethane diphosphonic acid (HEDP) and salts thereof.

The formulation of the first agent is not particularly limited; specific examples of the formulation include the formulations that are in a liquid state at 25° C. such as an aqueous solution or an emulsion; and the formulations that are in a gel state, a foam state, a cream state and a solid state at 25° C. Among these, the cream formulation is preferable from the viewpoint of exhibiting the application property to hair and the miscibility of different types of agents at the same time.

(Second Agent of Two-Part Type Oxidative Hair Dye)

The second agent may contain the foregoing solubilizer and the like in addition to the oxidant. The oxidant more improves the decolorization property for melanin contained in hair. Specific examples of the oxidant include hydrogen peroxide, urea peroxide, melamine peroxide, sodium percarbonate, potassium percarbonate, sodium perborate, potassium perborate, ammonium persulfate, potassium persulfate, sodium persulfate, sodium peroxide, potassium peroxide, magnesium peroxide, barium peroxide, calcium peroxide, strontium peroxide, hydrogen peroxide adducts of sulfates, hydrogen peroxide adducts of phosphates, and hydrogen peroxide adducts of pyrophosphates. Only one of these specific examples of the oxidant may be contained alone, or two or more of these specific examples may be contained in combination. The content of the oxidant in the second agent is appropriately set, and is preferably 0.1% by mass or more, more preferably 2% by mass or more, and furthermore preferably 3% by mass or more. When the content of the oxidant is 0.1% by mass or more, the decolorization property for melanin is more improved. The content of the oxidant in the second agent is preferably 15% by mass or less, more preferably 9% by mass or less, and furthermore preferably 6% by mass or less. When the content of the oxidant is 15.0% by mass or less, the damage of hair and the like can be more suppressed.

When hydrogen peroxide is mixed in the second agent as an oxidant, for the purpose of improving the stability of hydrogen peroxide, the second agent preferably contains a stabilizer such as sodium stannate, ethylene glycol phenyl ether (phenoxyethanol), hydroxyethane diphosphonic acid and a salt thereof. Examples of the hydroxyethane diphosphonic acid salt include tetrasodium hydroxyethane diphosphonate and disodium hydroxyethane diphosphonate. The second agent may contain the components that are generally contained in an oxidative hair dye and that do not disturbing the actions of the foregoing respective components. For example, the second agent may optionally contain the foregoing components contained in the first agent within the ranges not impairing the advantageous effects of the present invention.

The formulation of the second agent is not particularly limited; specific examples of the formulation include the formulations that are in a liquid state at 25° C. such as an aqueous solution or an emulsion; and the formulations that are in a gel state, a foam state, a cream state and a solid state at 25° C. When for the first agent a cream-state formulation is adopted, the formulation of the second agent is preferably a formulation in a liquid state such as an emulsion or a formulation in a cream state from the viewpoint of improving the miscibility with the first agent.

<Three-Part Type Oxidative Hair Dye>

For example, the first agent of the two-part type oxidative hair dye may be divided into an agent containing the alkaline agent and an agent containing the components other than the alkaline agent, and thus the oxidative hair dye may be constituted as a three-part oxidative hair dye. In this case, the three-part oxidative hair dye has satisfactory formulation stability. In this way, from the viewpoint of the formulation stability and the like, the respective components contained in the first agent or the second agent may be stored as divided into a plurality of agents. Even when the oxidative hair dye is constituted as a three or more part type, such an oxidative hair dye is still included in the present invention as long as the aforementioned oxidative hair dye achieves the advantageous effects of the present invention.

<Preparation of Oxidative Hair Dye Mixture>

In the oxidative hair dye, the foregoing respective agents are mixed with each other, and thus a mixture is prepared when the oxidative hair dye is used. In the preparation of the mixture, the mixture may be prepared by placing predetermined amounts of the respective agents in an airtight container having a predetermined volume and by shaking and mixing the respective agents together. Alternatively, the mixture may also be prepared by placing the respective agents in a vessel such as a tray and by stirring and mixing the respective agents together with a brush, a stirring rod, or the like. For example, in the case where the first agent is a cream formulation, and the second agent is a liquid formulation such as an emulsion or a cream formulation, a mixing by shaking by using a tubular airtight container having a volume of 100 to 300 mL is preferable from the viewpoint of easy mixing operation. The total volume of the mixture in the container is preferably 20 to 80% by volume based on the internal volume of the airtight container from the viewpoint of improving the miscibility. The shaking-mixing with an airtight container containing the respective agents placed therein may be performed by manual up-and-down/rightand-left reciprocating motion, or may be performed mechanically by using a vibration exciter or the like. The obtained mixture of the oxidative hair dye is applied to hair in a just necessary amount by using, for example, hands with thin gloves, a comb, or a brush, or a container with a lid having a discharge opening or with a comb. In the present invention, the operation such as combing after a predetermined elapsed time is also included in the application operation.

The oxidative hair dye according to the present embodiment achieves the following advantages.

(1) The oxidative hair dye according to the present embodiment comprises (A) a cellulose derivative and (B) a polyethylene glycol having a number average molecular weight of 2,000 or less, in a predetermined proportion. The (A) component improves the spreadability of the mixture, and improves the application property to hair when the mixture is applied to hair with a brush or the like; and the (B) component suppresses the degradation with time of the application property during use. In this way, the uniformly-dyeing property is also improved.

(2) In the present embodiment, when a higher alcohol that is in the liquid state at 25° C. is used as the (C) component, the formulation stability is more improved.

(3) When hydroxy ethyl cellulose is used as the (A) component, and the first agent is formed as a cream formulation, the stability of the hydroxy ethyl cellulose is more improved.

(4) When a tubular airtight container having a volume of 100 to 300 mL is used in the operation of shaking-mixing the first agent and the second agent, and the proportion of the total volume of the mixture is 20 to 80% by volume based on the internal volume of the container, the miscibility at the time of use is more improved.

(5) When the airtight container containing the respective agents is manually shaken by reciprocating motion in the up-and-down direction to mix the respective agents with each other, a mixture can be prepared easily and in a short time.

The above-described embodiment may be modified as follows.

The above-described multiple part-type oxidative hair dye may be constituted as a multiple part-type hair bleaching/dye removing agent, by omitting the mixing of the oxidative dye. Even in such a constitution, the (A) component improves the spreadability of the mixture and thus improves the application property to hair when the mixture is applied to hair with a brush or the like, and the (B) component suppresses the degradation with time of the application property during use. In this way, the uniformity of bleaching/dye removing is also improved.

The viscosity range of the first agent or the second agent is not particularly limited; however, in the case of an emulsion formulation, the viscosity at 25° C. is preferably 3,000 to 10,000 millipascal second (mPa·s), and in the case of a cream or gel formulation, the viscosity at 25° C. is preferably 10,000 to 50,000 mPa·s. A viscosity can be determined by using, for example, a B-type viscometer under the measurement conditions of 25° C. and 1 minute. Specific examples of the B-type viscometer include a BL-type viscometer (manufactured by Toki Sangyo Co., Ltd.). The rotor used and the rotation speed are appropriately selected according to the measurable viscosity range of the measurement apparatus. For example, a viscosity can be determined by using a size 3 rotor under the condition of 120 rpm.

The hair cosmetic composition of the embodiment achieves the advantageous effects of the present invention when the (A) to (C) components are contained in the mixture at the time of use. Accordingly, when the hair cosmetic composition is constituted as a two or more part-type formulation, the (A) to (C) components may be contained in any of the agents during storage.

In the embodiment, some of the components contained in the first agent, the second agent, or the third agent of the hair cosmetic composition may constitute an additional agent to increase the number of the agents constituting the hair cosmetic composition.

In the embodiment, a direct dye listed in, for example, "The Japanese Standards of Quasi-Drug Ingredients" (published by Yakuji Nippo Ltd., June 2006) may be optionally contained as a dye other than the foregoing oxidative dye, within a range not impairing the advantageous effects of the present invention.

EXAMPLES

Next, the foregoing embodiments will be described more specifically with reference to Examples and Comparative Examples. The present invention is not limited to the constitutions described in the Examples section.

Test Example 1: Oxidative Hair Dye

As an oxidative hair dye, a first agent in a cream state containing the respective components shown in Tables 1 and 2, and a second agent in a cream state containing the respective components shown in Table 3 were prepared. The numerical values in the rows of the respective components in Tables 1 to 4 show the contents of the components concerned and the units thereof are percent by mass. The symbols (A) to (C) in the "Components" columns in the tables represent the compounds corresponding to the respective components described in the claims of the present application. The symbol "b" in the "Components" column in the table represents a compound for comparison with the component described in the claims of the present application.

Next, in each of Examples and Comparative Examples, the first agent and the second agent of the oxidative hair dye were mixed with each other in a ratio of 2:3 to prepare a mixture of the oxidative hair dye. The mixing of the first agent and the second agent was performed by using a cylindrical airtight lidded container (internal volume: 200 mL) of 12 cm in height and 4.5 cm in diameter. The container was charged with a total volume of 100 mL of the first agent and the second agent, and then the container was shaken in an up-and-down direction 30 times as reciprocating motion, and thus, the first and second agents were mixed with each other.

Next, to hair tuft samples (manufactured by Beaulax Co., Ltd.) of white hairs, black hairs and a mixture of black hairs and white hairs (proportion of white hairs: 30%) of 10 cm in length (hereinafter, simply referred to as hair tufts), the mixture was applied by using a brush, and the hair tufts were allowed to stand at room temperature (30° C.) for 25 minutes. Next, the oxidative hair dye attached to the hair tufts was washed away with water, then the hair tufts were shampooed twice (by using Bigen treatment shampoo manufactured by Hoyu Co., Ltd.) and conditioned once (by using Bigen treatment conditioner manufactured by Hoyu Co., Ltd.). Subsequently, the hair tufts were blow-dried with warm air, and then allowed to stand for a day. The hair tufts subjected to the hair dyeing treatment were evaluated for the hair dyeing property according to the following method. In addition, the application property at the time of applying the mixture to each of the hair tufts was evaluated immediately after the preparation of the mixture and after a predetermined time elapsed after the preparation of the mixture.

(Application Property of Mixture Immediately after Preparation)

Five panelists evaluated the application property of the mixture of each of Examples and Comparative Examples on the basis of the following standards, and thus determined whether or not the application property immediately after the preparation of the mixture was excellent. The spreadability of the mixture was scored on the basis of the following 5-point scale: excellent (5 points), good (4 points), fair (3 points), slightly poor (2 points), and poor (1 point). The scoring results of the panelists were averaged; the mixture was rated as "excellent: 5", "good: 4", "fair: 3", "slightly poor: 2", or "poor: 1" when the average score was 4.6 points or more, 3.6 points or more and less than 4.6 points, 2.6 points or more and less than 3.6 points, 1.6 points or more and less than 2.6 points, or less than 1.6 points, respectively; thus, the evaluation results were obtained. The results thus obtained are shown in the tables below.

(Application Property after Predetermined Elapsed Time)

Five panelists evaluated the application property of the mixture of each of Examples and Comparative Examples after 25 minutes from the preparation of the mixture, on the basis of the following standards, and thus determined whether or not the application property after 25 minutes from the preparation of the mixture is excellent. The mixture-applied hair tufts were subjected to combing after 20 minutes from the completion of the application, the drying condition of the mixture and the degree of the smoothness of the combing operation were comprehensively evaluated on the basis of the following 5-point scale; excellent (5 points), good (4 points), fair (3 points), slightly poor (2 points), and poor (1 point). The scoring results of the panelists were averaged; the mixture was rated as "excellent: 5", "good: 4", "fair: 3", "slightly poor: 2", or "poor: 1" when the average score was 4.6 points or more, 3.6 points or more and less than 4.6 points, 2.6 points or more and less than 3.6 points, 1.6 points or more and less than 2.6 points, or less than 1.6 points, respectively; thus, the evaluation results were obtained. The results thus obtained are shown in the tables below.

(Hair Dyeing Property)

Five panelists visually evaluated, under a standard light source, the tint of the hair tufts of each of Examples and Comparative Examples after the hair dyeing treatment on the basis of the following standards, and thus determined whether or not the hair dyeing property is excellent. The tint was scored on the basis of the following 5-point scale; excellent (5 points), good (4 points), fair (3 points), slightly poor (2 points), and poor (1 point). The scoring results of the panelists were averaged; the mixture was rated as "excellent: 5", "good: 4", "fair: 3", "slightly poor: 2", or "poor: 1" when the average score was 4.6 points or more, 3.6 points or more and less than 4.6 points, 2.6 points or more and less than 3.6 points, 1.6 points or more and less than 2.6 points, or less than 1.6 points, respectively; thus, the evaluation results were obtained. The results thus obtained are shown in the tables below.

TABLE 1

| | Components of first agent | Example 1 | Example 2 | Example 3 | Example 4 | Example 5 | Example 6 | Example 7 |
|---|---|---|---|---|---|---|---|---|
| | Cetanol | 1.5 | 1.5 | 1.5 | 1.5 | 1.5 | 1.5 | 1.5 |
| | Stearyl alcohol | 7 | 7 | 7 | 7 | 7 | 7 | 7 |
| | Vaseline | 1 | 1 | 1 | 1 | 1 | 1 | 1 |
| | POE(4) stearyl ether | 2.5 | 2.5 | 2.5 | 2.5 | 2.5 | 2.5 | 2.5 |
| | POE(20) cetyl ether | 2 | 2 | 2 | 2 | 2 | 2 | 2 |
| | POE(50) oleyl ether | 1 | 1 | 1 | 1 | 1 | 1 | 1 |
| | Behenyl trimethyl ammonium chloride (number of carbon atoms: 22) | 1 | 1 | 1 | 1 | 1 | 1 | 1 |
| (A) | Hydroxyethyl cellulose | 0.5 | 0.25 | 1 | — | 0.5 | 0.5 | 0.5 |
| (A) | Cationized cellulose | — | — | — | 0.5 | — | — | — |
| (B) | Polyethylene glycol (number average molecular weight: 400) | 7 | 7 | 7 | 7 | 2 | 16 | — |
| (B) | Polyethylene glycol (number average molecular weight: 1540) | — | — | — | — | — | — | 7 |
| (C) | 2-Octyldodecanol | 1 | 1 | 1 | 1 | 1 | 1 | 1 |
| | Polydimethylmethylene piperidinium chloride solution (40% by mass) | 1 | 1 | 1 | 1 | 1 | 1 | 1 |
| | Trisodium hydroxyethyl ethylenediamine triacetate solution (40% by mass) | 0.5 | 0.5 | 0.5 | 0.5 | 0.5 | 0.5 | 0.5 |
| | Anhydrous sodium sulfite (10% by mass) | 2 | 2 | 2 | 2 | 2 | 2 | 2 |
| | p-Toluylenediamine sulfate | 1 | 1 | 1 | 1 | 1 | 1 | 1 |
| | Resorcin | 0.5 | 0.5 | 0.5 | 0.5 | 0.5 | 0.5 | 0.5 |
| | p-Aminophenol | 0.6 | 0.6 | 0.6 | 0.6 | 0.6 | 0.6 | 0.6 |
| | 5-Amino-o-cresol | 0.3 | 0.3 | 0.3 | 0.3 | 0.3 | 0.3 | 0.3 |
| | L-Ascorbic acid | 0.3 | 0.3 | 0.3 | 0.3 | 0.3 | 0.3 | 0.3 |

TABLE 1-continued

|  | Components of first agent | Example 1 | Example 2 | Example 3 | Example 4 | Example 5 | Example 6 | Example 7 |
|---|---|---|---|---|---|---|---|---|
|  | 28% by mass Ammonia water | 2 | 2 | 2 | 2 | 2 | 2 | 2 |
|  | 70% by mass Monoethanolamine | 13 | 13 | 13 | 13 | 13 | 13 | 13 |
|  | Purified water | Balance | Balance | Balance | Balance | Balance | Balance | Balance |
|  | Total | 100 | 100 | 100 | 100 | 100 | 100 | 100 |
|  | Content of A component in mixture | 0.2 | 0.1 | 0.4 | 0.2 | 0.2 | 0.2 | 0.2 |
|  | Content of B component in mixture | 2.8 | 2.8 | 2.8 | 2.8 | 0.8 | 6.4 | 2.8 |
|  | Content of B component/content of A component | 14 | 28 | 7 | 14 | 4 | 32 | 14 |
|  | Evaluations |  |  |  |  |  |  |  |
|  | Application property of mixture immediately after preparation | 5 | 4 | 5 | 5 | 5 | 5 | 5 |
|  | Application property after predetermined elapsed time | 4 | 4 | 4 | 3 | 3 | 5 | 4 |
|  | Hair dyeing property | 5 | 5 | 5 | 5 | 5 | 3 | 5 |

TABLE 2

|  | Components of first agent | Example 8 | Example 9 | Example 10 | Comparative Example 1 | Comparative Example 2 | Comparative Example 3 |
|---|---|---|---|---|---|---|---|
|  | Cetanol | 1.5 | 1.5 | 2.5 | 1.5 | 1.5 | 1.5 |
|  | Stearyl alcohol | 7 | 7 | 7 | 7 | 7 | 7 |
|  | Vaseline | 1 | 1 | 1 | 1 | 1 | 1 |
|  | POE(4) stearyl ether | 2.5 | 2.5 | 2.5 | 2.5 | 2.5 | 2.5 |
|  | POE(20) cetyl ether | 2 | 2 | 2 | 2 | 2 | 2 |
|  | POE(50) oleyl ether | 1 | 1 | 1 | 1 | 1 | 1 |
|  | Behenyl trimethyl ammonium chloride (number of carbon atoms: 22) | 1 | 1 | 1 | 1 | 1 | 1 |
| (A) | Hydroxyethyl cellulose | 0.5 | 0.5 | 0.5 | — | 0.5 | 0.5 |
| (B) | Polyethylene glycol (number average molecular weight: 400) | 7 | 7 | 7 | 7 | — | — |
| b | High-polymerization polyethylene glycol (number average molecular weight: 400,000) | — | — | — | — | — | 7 |
| (C) | 2-Octyldodecanol | — | — | — | 1 | 1 | 1 |
| (C) | Oleyl alcohol | 1 | — | — | — | — | — |
| (C) | Oleic acid | — | 1 | — | — | — | — |
|  | Polydimethylmethylene piperidinium chloride solution (40% by mass) | 1 | 1 | 1 | 1 | 1 | 1 |
|  | Trisodium hydroxyethyl ethylenediamine triacetate solution (40% by mass) | 0.5 | 0.5 | 0.5 | 0.5 | 0.5 | 0.5 |
|  | Anhydrous sodium sulfite (10% by mass) | 2 | 2 | 2 | 2 | 2 | 2 |
|  | p-Toluylenediamine sulfate | 1 | 1 | 1 | 1 | 1 | 1 |
|  | Resorcin | 0.5 | 0.5 | 0.5 | 0.5 | 0.5 | 0.5 |
|  | p-Aminophenol | 0.6 | 0.6 | 0.6 | 0.6 | 0.6 | 0.6 |
|  | 5-Amino-o-cresol | 0.3 | 0.3 | 0.3 | 0.3 | 0.3 | 0.3 |
|  | L-Ascorbic acid | 0.3 | 0.3 | 0.3 | 0.3 | 0.3 | 0.3 |
|  | 28% by mass Ammonia water | 2 | 2 | 2 | 2 | 2 | 2 |
|  | 70% by mass Monoethanolamine | 13 | 13 | 13 | 13 | 13 | 13 |
|  | Purified water | Balance | Balance | Balance | Balance | Balance | Balance |
|  | Total | 100 | 100 | 100 | 100 | 100 | 100 |
|  | Content of A component in mixture | 0.2 | 0.2 | 0.2 | 0 | 0.2 | 0.2 |
|  | Content of B component in mixture | 2.8 | 2.8 | 2.8 | 2.8 | 0 | 0 |

TABLE 2-continued

| Components of first agent | Example 8 | Example 9 | Example 10 | Comparative Example 1 | Comparative Example 2 | Comparative Example 3 |
|---|---|---|---|---|---|---|
| Content of B component/content of A component | 14 | 14 | 14 | — | — | — |
| Evaluations | | | | | | |
| Application property of mixture immediately after preparation | 5 | 5 | 5 | 1 | 5 | — |
| Application property after predetermined elapsed time | 4 | 4 | 3 | 5 | 1 | — |
| Hair dyeing property | 5 | 5 | 5 | 5 | 5 | — |

TABLE 3

Components of second agent (cream state)

| | |
|---|---|
| 35% by mass Hydrogen peroxide | 15 |
| Cetanol | 5 |
| Isostearyl alcohol | 0.2 |
| POE(2) stearyl ether | 0.5 |
| POE(30) cetyl ether | 0.5 |
| Stearyl trimethyl ammonium chloride | 0.3 |
| Phenoxyethanol | 0.1 |
| Purified water | Balance |
| Total | 100 |

TABLE 4

Components of second agent (emulsion formulation)

| | |
|---|---|
| 35% by mass Hydrogen peroxide | 15 |
| Cetanol | 1 |
| POE(2) stearyl ether | 0.2 |
| POE(30) cetyl ether | 0.2 |
| Stearyl trimethyl ammonium chloride | 0.2 |
| Hydroxyethane diphosphonic acid | 0.05 |
| Tetrasodium hydroxyethane diphosphonate | 0.05 |
| Purified water | Balance |
| Total | 100 |

As shown in Tables 1 and 2, each of Examples was determined to have the results that each of the evaluation items was rated as 3 or higher. As shown in Table 2, Comparative Example 1, which did not contain the (A) component, was determined to be poor in the spreadability of the mixture, and to be poor in the application property immediately after the preparation of the mixture, as compared with each of Examples. Comparative Example 2, which did not contain the (B) component, was determined to be poor in the evaluation of the application property after the predetermined elapsed time as compared with each of Examples. Comparative Example 3 using a high-polymerization polyethylene glycol (number average molecular weight 400,000) in place of the (B) component was remarkably poor in the solubility to a solvent so as to generate undissolved lump (undissolved residue), and consequently no evaluation tests were performed. From Examples 1 and 6 and Comparative Example 1, the degradation with time of the application property in the case of the use of a cellulose derivative was determined to be suppressed by increasing the mixing amount of the (B) component.

When the oxidative hair dye of each of the foregoing Examples and Comparative Examples was evaluated under the condition that the second agent in a cream state shown in Table 3 was replaced with the second agent being an emulsion formulation, the same evaluations as shown in Tables 1 and 2 were achieved. It is to be noted that the second agent being an emulsion formulation used in the tests was prepared by mixing the components shown in Table 4.

Test Example 2: Bleaching Agent

In each of the first agents of the oxidative hair dyes of Examples 1 and 9 shown in Table 1, the addition of the dye was omitted, and thus the first agents (Examples 1-2 and 9-2) of the bleaching agents were prepared. By using such bleaching agents, in combination with the second agent being the emulsion formulation shown in Table 4, the hair tufts were subjected to a bleaching treatment by the same method as described above. The obtained hair tufts were evaluated, on the basis of the same standards as the standards for the hair dyeing property, with respect to whether or not the bleaching property was achieved.

The results showed that Example 9-2 was poor as compared with Example 1-1 in the evaluation of the bleaching property.

Test Example 3: Stability of First Agent of Oxidative Hair Dye

The stability of the first agent of each of the oxidative hair dyes of Examples 1 and 9 was evaluated. The first agent of each of Examples 1 and 9 was placed in a glass bottle, and stored in a thermostatic chamber at 60° C. for 24 hours, then the separation state of the first agent was visually evaluated, and thus, it was determined whether or not the retention effect of the first agent that is in the cream state was satisfactory.

The results showed that Example 9 was poor in the stability of the first agent as compared with Example 1.

The foregoing embodiment and Examples are presented as exemplification for describing the present invention, and the present invention is not limited to the foregoing embodiment and Examples. For the embodiment disclosed for exemplification, various alternatives, alterations and modifications can be made without departing from the gist and scope of the present invention. For example, the subject of the present invention may possibly reside in features smaller in number than all the features of the particular disclosed embodiment. Accordingly, the scope of the claims of the invention is incorporated into the detailed description, and each of the claims itself claims a separate embodiment. The scope of the present invention is intended to include, in the scope of the claims, all of such alternative forms, alteration forms and modification forms, together with all the equivalents of these forms.

The invention claimed is:

1. A hair cosmetic composition comprising an alkaline agent and an oxidant, and being constituted as a hair dye or a hair bleaching/dye removing agent, the hair cosmetic composition further comprising:
   (A) a cellulose derivative in a content of 0.01 to 1% by mass; and
   (B) a polyethylene glycol having a number average molecular weight of 400 to 2,000, wherein the mass ratio of the content of the (B) component to the content of the (A) component is 1 to 50.

2. The hair cosmetic composition according to claim 1, further comprising (C) at least one oily component that is in a liquid state at 25° C. and is selected from the group consisting of a higher alcohol, an oil/fat, a hydrocarbon, a higher fatty acid, and a wax.

3. The hair cosmetic composition according to claim 2, wherein the (C) component comprises a higher alcohol that is in a liquid state at 25° C.

4. The hair cosmetic composition according to claim 1 comprising:
   a first agent containing the alkaline agent and the (A) component; and
   a second agent containing the oxidant,
   wherein the hair cosmetic composition is applied to hair after the first agent and the second agent are shaken and mixed with each other in an airtight container.

* * * * *